United States Patent [19]

Kishino et al.

[11] 4,290,978
[45] Sep. 22, 1981

[54] PRODUCTION OF PHOSPHORO CHLORIDE THIOLATES

[75] Inventors: Shigeo Kishino; Junichi Saito; Toyohiko Kume; Kunihiro Isono, all of Tokyo, Japan

[73] Assignee: Nihon Tokushu Noyasu Seizo K.K., Tokyo, Japan

[21] Appl. No.: 131,714

[22] Filed: Mar. 19, 1980

[30] Foreign Application Priority Data

Apr. 19, 1979 [JP] Japan .................................. 54-47192

[51] Int. Cl.³ .............................................. C07F 9/20
[52] U.S. Cl. ..................................... 260/973; 260/960
[58] Field of Search ................................ 260/960, 973

[56] References Cited

U.S. PATENT DOCUMENTS

| | | | |
|---|---|---|---|
| 3,082,239 | 5/1963 | Muhlmann et al. | 260/960 |
| 3,337,658 | 8/1967 | Senkbeil et al. | 260/960 |
| 3,454,679 | 7/1969 | Aichenegge et al. | 260/960 |
| 4,056,581 | 11/1977 | Bayer et al. | 260/960 |
| 4,118,435 | 10/1978 | Kleinstück et al. | 260/960 |

FOREIGN PATENT DOCUMENTS 1159935 9/1964 Fed. Rep. of Germany .
1158709 7/1969 United Kingdom ................ 260/960

OTHER PUBLICATIONS

Houben-Weyl, vol. 12, No. 2, pp. 45,50-51.
Zhur. Obschshei Kim., vol. 26, 3381-3384.

Primary Examiner—Anton H. Sutto

[57] ABSTRACT

A process for the production of a phosphoro chloride thiolate of the formula

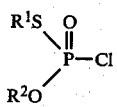

wherein
$R^1$ is alkyl, alkoxyalkyl, aryl, or aryl substituted by alkyl, alkoxy or halogen, and
$R^2$ is alkyl,
comprising reacting a mixture of a dialkyl chlorophosphite of the formula $(R^2O)_2PCl$ and an alkyl dichloro-phosphite of the formula $(R^2O)PCl_2$ with a sulphenyl chloride of the formula $R^1SCl$ to produce a mixture of a phosphorochloridothiolate of the formula

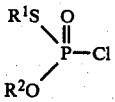

and a phosphorodichloridothiolate of the formula

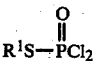

and reacting the mixture without isolation with an alcohol of the formula $R^2OH$ in the presence of a dehydrochlorinating agent thereby to convert the phosphorodichloridothiolate of the formula

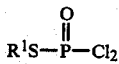

to additional phosphorochloridothiolate

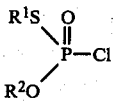

The starting mixture is produced by reacting phosphorus trichloride with a trialkyl phosphite, or with an alcohol in the presence of a dehydrochlorinating agent.

7 Claims, No Drawings

PRODUCTION OF PHOSPHORO CHLORIDE THIOLATES

The present invention relates to an unobvious process for the production of certain phosphorochloridothiolates which can be used as the starting materials for certain organic phosphate esters that are useful as agricultural chemicals.

A process for producing phosphorochloridothiolates is disclosed in U.S. Pat. No. 3,082,239, which gives the following reaction:

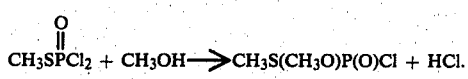

$$CH_3SPCl_2 + CH_3OH \longrightarrow CH_3S(CH_3O)P(O)Cl + HCl. \quad (I)$$

The S-methyl phosphorodichloridothiolate which is required for the above reaction may be produced by the isomerization reaction of O-methyl phosphorodichloridothionate according to U.S. Pat. No. 3,337,658, as shown by the following reaction:

$$\underset{\|}{\overset{S}{CH_3OPCl_2}} \longrightarrow \underset{\|}{\overset{O}{CH_3SPCl_2}}. \quad (i)$$

Since it is difficult to control the temperature in the isomerization reaction, including the cases of alkyl groups other than methyl, and since about 10% of a by-product S-alkyl phosphorodichloridedithioate is produced, this process is not suitable for producing O-alkyl-S-alkylphosphoro chloride thiolates in high purity on a commercial scale.

In addition, G. Schrader et al have suggested in West German Pat. No. 1,159,935 that phosphorodichloridothiolates may be synthesized by the following reaction:

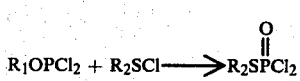

$$R_1OPCl_2 + R_2SCl \longrightarrow R_2SPCl_2 \quad (ii)$$

wherein
R₁ represents alkyl and
R₂ represents alkyl.

This process, too, is not advantageous for commercial production, because it entails the isolation of the alkyl dichlorophosphites as a prerequisite.

Another process for producing phosphorochloridothiolates has been disclosed in Zhur. Obschchei Kim. Vol. 26, 3381–3384, the reaction of which proceeds as follows:

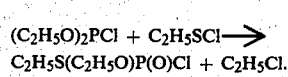

$$(C_2H_5O)_2PCl + C_2H_5SCl \longrightarrow \quad (II)$$
$$C_2H_5S(C_2H_5O)P(O)Cl + C_2H_5Cl. \quad (II)$$

However, it is difficult to obtain not only the raw material, diethyl chlorophosphite, but also other lower dialkyl chlorophosphites of high purity in high yields. For example, in order to produce the said dialkyl chlorophosphites, the following reactions have been disclosed in Methoden der Organischen Chemie XII/2 50, 45:

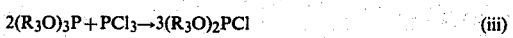

$$2(R_3O)_3P + PCl_3 \rightarrow 3(R_3O)_2PCl \quad (iii)$$

$$PCl_3 + 2R_3OH \rightarrow (R_3O)_2PCl + 2HCl \quad (iv)$$

wherein
R₃ represents alkyl.

In the above reaction (iii), 0.5 mole of phosphorus trichloride is used per mole of the trialkyl phosphite, and in the reaction (iv) 2 moles of the alcohol and 2 moles of a dehydrochlorinating agent are reacted with 1 mole of phosphorus trichloride. In either synthetic process, since the trialkyl phosphite and the alkyl dichlorophosphite (R₃OPCl₂) are always present as impurities, the separation of the desired dialkyl chlorophosphite is difficult even by distillation, because it is unstable and it has a similar vapor pressure similar to those of the other components and azeotropic properties; a great reduction in yield occurs as a result. In particular, the trialkyl phosphite rapidly reacts with a sulphenyl chloride in the subsequent reaction shown as follows:

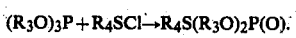

$$(R_3O)_3P + R_4SCl \rightarrow R_4S(R_3O)_2P(O).$$

The undesired by-product R₄S(R₃O)₂P(O) greatly diminishes the purity and yield of the required final product, the phosphorochloridothiolate.

The present invention now provides a process for producing a phosphorochloridothiolate of the general formula:

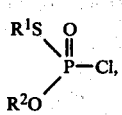

$$\begin{array}{c} R^1S \\ \phantom{R^1S}\diagdown \\ \phantom{R^1S}\phantom{\diagdown}P-Cl, \\ \phantom{R^1S}\diagup \\ R^2O \end{array} \quad (V)$$

wherein
R¹ represents alkyl, alkoxyalkyl or aryl that is optionally substituted by alkyl, alkoxy or halogen, and
R² represents alkyl, (a) characterized in that a trialkyl phosphite of the general formula $$(R^2O)_3P \quad (I),$$

wherein
R² is as defined above,
is reacted with phosphorus trichloride to produce a mixture of a dialkyl chlorophosphite of the general formula $$(R^2O)_2PCl \quad (II),$$

wherein
R² is as defined above,
and an alkyl dichlorophosphite of the general formula $$(R^2O)PCl_2 \quad (III),$$

wherein
R² is as defined above,
the resulting mixture is reacted with a sulphenyl chloride of the general formula $$R^1SCl \quad (IV),$$

wherein
R¹ is as defined above,
to produce a mixture of a phosphorochloridothiolate of the general formula

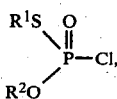 (V)

wherein
R¹ and R² are as defined above,
and a phosphorodichloridothiolate of the general formula

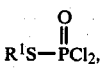 (VI)

wherein
R¹ is as defined above,
and the phosphorodichloridothiolate in the mixture is reacted, without isolation from the mixture, with an alcohol of the general formula

R²OH (VII), wherein
R² is as defined above,
in the presence of a dehydrochlorinating agent to produce the compound of the formula (V), or (b) characterized in that phosphorus trichloride is reacted with an alcohol of the general formula

R²OH (VII), wherein
R² is as defined above,
in the presence of a dehydrochlorinating agent to produce a mixture of a dialkyl chlorophosphite of the general formula (R²O)₂PCl (II), wherein
R² is as defined above,
and an alkyl dichlorophosphite of the general formula (R²O)PCl₂ (III), wherein
R² is as defined above,
the resulting mixture is reacted with a sulphenyl chloride of the general formula R¹SCl (IV), wherein
R¹ is as defined above,
to produce a mixture of a phosphorochloridothiolate of the general formula

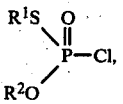 (V)

wherein
R¹ and R² are as defined above,
and a phosphorodichloridothiolate of the general formula

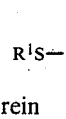 (VI)

wherein
R¹ is as defined above,
and the phosphorodichloridothiolate in the mixture is reacted, without isolation from the mixture, with an alcohol of the general formula

R²OH (VII), wherein
R² is as defined above,
in the presence of a dehydrochlorinating agent to produce the compound of the formula (V).

Thus, it has been discovered that a mixture of the alkyl dichlorophosphite and the dialkyl chlorophosphite with an extremely low content of the trialkyl phosphite can be obtained either by reacting the trialkyl phosphite of the formula (I) with about 0.6–1.5 times the molar amount of phosphorus trichloride and at a temperature from about −30° to 100° C., or by reacting phosphorus trichloride with about 1.2–1.8 times the molar amount of an alcohol of the formula (VII) in the presence of a dehydrochlorinating agent (the dehydrochlorinating agent preferably being a base present in molar amount equal to that of the alcohol) and at a temperature from about −30° to 100° C.

It has further been discovered that when the reaction mixture of the dialkyl chlorophosphite of the formula (II) and the alkyl dichlorophosphite of the formula (III) is reacted with a sulphenyl chloride of the formula (IV) until the orange to reddish orange color of the sulphenyl chloride disappears, the dialkyl chlorophosphite and the alkyl dichlorophosphite are converted substantially quantitatively to the desired phosphorochloridothiolate of the formula (V) and the phosphorodichloridothiolate of the formula (VI) respectively and the formation of by-products is greatly suppressed.

It has also been discovered that the phosphorochloridothiolate and phosphoro dichloridothiolate thus obtained can be quantitatively analyzed by gas chromatography, so that the phosphorodichloridothiolate thus determined without any separation can be reacted with, preferably, the equimolar amount of the alcohol of the formula (VII) and preferably the equimolar amount of the dehydrochlorinating agent in the presence of an appropriate solvent, at a temperature from about −20° to 50° C., selectively to esterify the phosphorodichloridothiolate to the final product, the phosphorochloridothiolate. Under these optimum reaction conditions, substantially no formation of the phosphorothiolate due to the reaction of the phosphoro chloridothiolate and the alcohol was observed, although such a reaction could well have been expected.

In accordance with the present invention, it is possible readily and selectively to produce the desired phosphoro chloridothiolate by the given sequence of reactions, without separating the reaction product from each step. The present process permits the commercially feasible and advantageous production of the compounds (V).

The reaction sequence in the process of the present invention can be illustrated as follows:

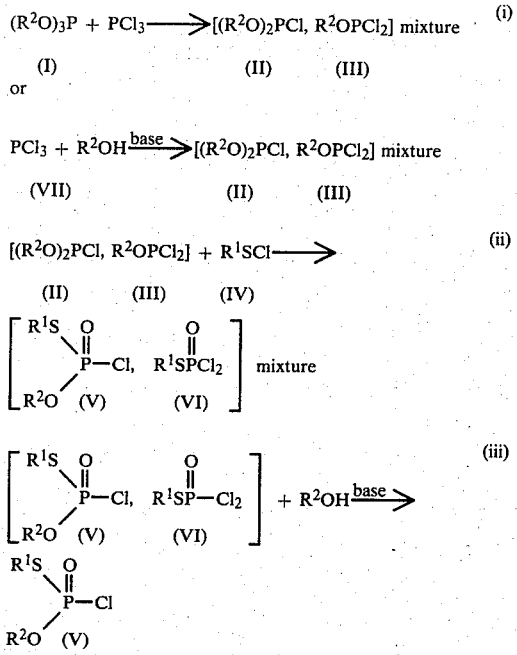

In the above equations, $R^1$ and $R^2$ have the meanings given above.

Preferably, $R^1$ represents methyl, ethyl, n- or isopropyl, n-, iso-, sec- or tert.-butyl, n- or iso-amyl, n-hexyl, methoxymethyl, ethoxymethyl, n- or isopropoxymethyl, n-, iso-, sec- or tert-butoxymethyl, 2-methoxyethyl, 2-ethoxyethyl, 2-n- or iso-propoxyethyl, 2-n-, iso-, sec- or tert-butoxyethyl, 3-methoxypropyl, 3-ethoxypropyl or phenyl or naphthyl, either of which may optionally carry one or more substituents selected from methyl, ethyl, n- or iso-propyl, n-, iso-, sec- or tert-butyl, n- or iso-amyl, n-hexyl, methoxy, ethoxy, n- or iso-propoxy, n-, iso-, sec- or tert-butoxy, chlorine, fluorine, bromine and iodine.

Preferably, $R^2$ represents methyl, ethyl, n- or isopropyl, n-, iso-, sec- or tert-butyl, n- or iso-amyl or n-hexyl.

The following are examples of the trialkyl phosphites of the formula (I): trimethyl phosphite, triethyl phosphite, tri-n- (or iso-) propyl phosphite and tri-n- (iso-, sec- or tert-) butyl phosphite.

Examples of the sulphenyl chlorides of the formula (IV) are: methyl-, ethyl-, n- (or iso-) propyl, n- (iso-, sec- or tert-)-butyl, n- or iso-amyl, and n-hexyl-sulphenyl chlorides; methoxymethyl-, ethoxymethyl-, n- (or iso-) propoxymethyl-, n- (iso-, sec- or tert-) butoxymethyl-,2-methoxyethyl-, 2-ethoxyethyl-, 2-n- (and iso-) propoxyethyl-, 2-n- (iso-, sec- or tert-) butoxyethyl, 3-methoxypropyl- and 3-ethoxypropyl-sulphenyl chlorides; 2- (3- or 4-) methyl-, [ethyl-, or n- (or iso-) propyl-, or n- (iso-, sec- and tert-) butyl-] phenylsulphenyl chlorides; 2,3- (2,4-, 2,5-, 2,6-, 3,4- or 3,5-) dimethyl- [diethyl-, di-n- (or iso-) propyl-, or di-n- (iso-, sec- and tert-) butyl] phenyl-sulphenyl chlorides; 2- (3- or 4-) methoxy- [ethoxy-, n(or iso-) propoxy-, or n- (iso-, sec- and tert-) butoxy-] phenylsulphenyl chlorides; 2- (3- or 4-) chloro-(bromo-, fluoro- or iodo-) phenyl-sulphenyl chlorides; 2,3- (2,4-, 2,5-, 2,6-, 3,4- and 3,5-) dichloro- (dibromo-, difluoroor diiodo-) phenylsulphenyl chlorides; α- (or β-) naphthyl-sulphenyl chlorides; α-4-chloro-(or bromo-) naphthylsulphenyl chlorides; α-2- (or 4-) methylnaphthyl sulphenyl chlorides; and α-6-chloro- (bromo- or methyl-) naphthylsulphenyl chloride.

In the practice of the present invention, a solvent or a diluent may be employed if desired. For this purpose, any inert solvent or diluent can be used. Examples of such solvents and diluents are aliphatic, alicyclic and aromatic hydrocarbons (which may optionally be chlorinated) such as hexane, cyclohexane, petroleum ether, ligroin, benzene, toluene, xylenes, methylene chloride, chloroform, carbon tetrachloride, ethylene chloride, trichloroethylene and chlorobenzene; ethers such as diethyl ether, methyl ethyl ether, di-iso-propyl ether, dibutyl ether, propylene oxide, dioxane and tetrahydrofuran: ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulphones and sulphoxides such as dimethylsulphoxide and sulpholane; and organic bases such as pyridine.

As mentioned above, the process of the present invention is preferably carried out in the presence of an acid-binding agent, i.e. the dehydrochlorinating agent. Examples of such acid binders are the customary alcoholates and tertiary amines, such as triethylamine, dimethylbenzylamine, diethylaniline or pyridine.

The process of the present invention is illustrated by the following preparative examples, the identities of the products having been established by their mass spectra:

EXAMPLE 1

17.9 g (0.13 mole) of phosphorus trichloride were added to 33.2 g (0.2 mole) of triethyl phosphite at a temperature of not higher than 0° C. and the mixture was stirred at 55° C. for 2 hours. To the resulting mixture of ethyl dichlorophosphite and diethyl chlorophosphite was added a 35.5% solution of n-propylsulphenyl chloride in toluene at −20° C. until the mixture slightly assumed a reddish orange color due to n-propylsulphenyl chloride. The consumption of n-propylsulphenyl chloride in the above reaction was 0.325 mole. After stirring at room temperature for one hour, toluene was distilled off under a reduced pressure to obtain 65 g of a pale yellow liquid, which was found to contain the following components (analysis by gas chromatography):

S-n-propyl-phosphorodichloridothiolate: 23.7%
O-ethyl-S-n-propyl phosphorochloridothiolate: 72.2%
O,O-diethyl-S-n-propyl phosphorothiolate: 3.2%
di-n-propyl disulphide: 0.9%

The mixture was dissolved in 100 ml of toluene, the stoichiometric amounts of ethanol and triethylamine required to react with the S-n-propyl phosphorodichloridothiolate were added thereto dropwise at −20° C., and the mixture was stirred at room temperature for 3 hours. The resulting triethylamine hydrochloride was filtered off and toluene was distilled off under a reduced pressure to obtain 65 g of O-ethyl-S-n-propyl phosphorochloridothiolate. The purity was 92.9%. Therefore, the yield based on the total phosphorus used in the raw materials, i.e. triethyl phosphite and phosphorus trichloride, was 90% and that based on n-propylsulphenyl chloride was 92%. The boiling point of the O-ethyl-S-n-propyl phosphorochloridothiolate thus obtained was 67°–70° C./0.4 mmHg.

EXAMPLE 2

41.3 g (0.3 mole) of phosphorus trichloride were added to 33.2 g (0.2 mole) of triethyl phosphite at a temperature of not higher than 0° C. and the mixture was refluxed at about 100° C. for 3 hours, after which the same procedures as in Example 1 were followed to obtain 84 g of a mixture containing the following components:

S-n-propyl phosphorodichloridothiolate: 61.6%
O-ethyl-S-n-propyl phosphorochloridothiolate: 34.4%
O,O-diethyl-S-n-propyl phosphorothiolate: 3.1%
di-n-propyl disulphide: 0.9%

The S-n-propyl phosphorodichloridothiolate contained in the mixture was reacted with stoichiometric amounts of ethanol and triethylamine to obtain 87 g of O-ethyl-S-n-propyl phosphorochloridothiolate. The purity was 95.5%. Therefore, the yield based on the total phosphorus in the raw materials was 82%.

EXAMPLE 3

55 g (0.4 mole) of phosphorus trichloride were added dropwise to a toluene solution of 27.6 g (0.6 mole) of ethanol and 89.4 g (0.6 mole) of N,N-dimethylaniline at a temperature of not higher than 0° C. and the mixture was stirred at 85° C. for 30 minutes. After allowing to cool to room temperature, the resulting N,N-diethylaniline hydrochloride was filtered off to obtain a toluene solution containing ethyl dichlorophosphite and diethyl chlorophosphite. Thereafter, the same procedures as in Example 1 were followed to obtain 72 g of a mixture containing the following components:

S-n-propyl phosphorodichloridothiolate: 48.8%
O-ethyl-S-n-propyl phosphorochloridothiolate: 45.8%
O,O-diethyl-S-n-propyl phosphorothiolate: 3.6%
di-n-propyl disulphide: 1.6%

The S-n-propyl phosphorodichloridothiolate contained in the mixture was reacted with stoichiometric amounts of ethanol and triethylamine to obtain 75 g of O-ethyl-S-n-propyl phosphorochloridothiolate. The purity was 91.1%. Therefore, the yield based on the total phosphorus in the raw materials was 84%.

EXAMPLE 4

103 g (0.75 mole) of phosphorus trichloride were added to 166 g (1 mole) of triethyl phosphite at a temperature of not higher than 0° C. and the mixture was stirred at 55° C. for 2 hours to obtain a mixture of ethyl dichlorophosphite and diethyl chlorophosphite, a part of which was then added to a solution of 30.9 g (0.2 mole) of 2-n-propoxyethyl sulphenyl chloride in 50 ml of toluene at a temperature of not higher than 0° C. until the reddish orange color of 2-propoxyethylsulphenyl chloride disappeared. The total consumption of the mixture of ethyl dichlorophosphite and diethyl chlorophosphite in the above reaction was 32.8 g. The mixture was stirred for another 2 hours and toluene was distilled off under a reduced pressure to obtain 48 g of a mixture containing the following components:

S-2-n-propoxyethyl phosphorodichloridothiolate: 27.2%
O-ethyl-S-(2-n-propoxyethyl) phosphorochloridothiolate: 68.0%
O,O-diethyl-S-(2-n-propoxyethyl) phosphorothiolate: 4.8%

By procedures similar to those in Example 1, the mixture was reacted with the required amounts of ethanol and triethylamine to obtain 49 g of O-ethyl-S-(2-n-propoxyethyl) phosphorochloridothiolate. The purity was 93.2%. Therefore, the yield based on 2-propoxyethylsulphenyl chloride was 93%.

EXAMPLE 5

The mixture of ethyl dichlorophosphite and diethyl chlorophosphite obtained in Example 4 was added to a 100 ml of carbon tetrachloride solution containing 17.9 g (0.1 mole) of p-chlorophenyl sulphenyl chloride at a temperature of not higher than 0° C. to obtain 27 g of a mixture containing the following components:

S-p-chlorophenyl phosphorodichloridothiolate: 15.0%
O-ethyl-S-p-chlorophenyl phosphorochloridothiolate: 78.6%
O,O-diethyl-S-p-chlorophenyl phosphorothiolate: 6.3%

The mixture was reacted with the required amounts of ethanol and triethylamine to obtain 27 g of O-ethyl-S-(4-chlorophenyl) phosphorochloridothiolate. The purity was 93.0%. Therefore, the yield based on p-chlorophenyl sulphenyl chloride was 93%.

By similar procedures, the following compounds were synthesized with high purity and in high yield:

O-methyl-S-n-propyl posphorochloridothiolate, b.p. 68°–70° C./0.4 mmHg,
O-iso-propyl-S-n-propyl phosphorochloridothiolate, b.p. 70°–73° C./0.3 mmHg,
O-n-butyl-S-n-propyl phosphorochloridothiolate,
O-ethyl-S-iso-propyl phosphorochloridothiolate,
O-ethyl-S-n-butyl phosphorochloridothiolate,
O-ethyl-S-sec-butyl phosphorochloridothiolate,
O-ethyl-S-(2-methoxyethyl) phosphorochloridothiolate,
O-ethyl-S-(2-ethoxyethyl) phosphorochloridothiolate,
O-ethyl-S-(2-iso-propoxyethyl) phosphorochloridothiolate,
O-ethyl-S-(2-n-butoxyethyl) phosphorochloridothiolate,
O-ethyl-S-phenyl phosphorochloridothiolate, b.p. 116°–119° C./0.3 mmHg,
O-n-butyl-S-ethyl phosphorochloridothiolate, b.p. 89°–100° C./0.6 mmHg, and
O-iso-butyl-S-ethyl phosphorochloridothiolate, b.p. 79°–81° C./0.4 mmHg.

Comparison Example 1

According to a process by H. G. Cook et al, J.C.S. 1949 2921–2927, 27.5 g (0.2 mole) of phosphorus trichloride were added to 66.4 g (0.4 mole) of triethyl phosphite and the mixture was gently heated and refluxed for 30 minutes to obtain diethyl chlorophosphite, to which a solution of 66.3 g (0.6 mole) of n-propylsulphenyl chloride in toluene was added at −10° C. and the mixture was stirred at room temperature for a hour. Toluene was then distilled off to obtain 121 g of a reaction mixture which contained the following components:

S-n-propyl phosphorodichloridothiolate: 8.9%
O-ethyl-S-n-propyl phosphorochloridothiolate: 69.9%
O,O-diethyl-S-n-propyl phosphorothiolate: 15.8%
di-n-propyl disulphide: 5.4%

The mixture was reacted with required amounts of ethanol and triethylamine as in Example 1 to obtain 121 g of O-ethyl-S-n-propyl phosphorochloridothiolate. The purity was 78.1%. Therefore, the yield based on the total phosphorus and that based on the n-propylsulphenyl chloride were both 78%.

Comparison Example 2

In accordance with the procedures in Example 2, a mixture of diethyl chlorophosphite and ethyl dichlorophosphite was obtained from 33.2 g (0.2 mole) of triethyl phosphite and 41.3 g (0.3 mole) of phosphorus trichloride. A solution of 55.3 g (0.5 mole) of n-propylsulphenyl chloride in toluene was added dropwise to the above mixture at −20° C. and stirred at room temperature for 2 hours, after which toluene was distilled off under a reduced pressure to obtain 88 g of a reaction mixture which contained the following components:
S-n-propyl phosphorodichloridothiolate: 57.6%
O-ethyl-S-n-propyl phosphorochloridothiolate: 33.9%
O,O-diethyl-S-n-propyl phosphorothiolate: 2.9%
di-n-propyl disulphide: 56.6%

The mixture was then reacted with the required amounts of ethanol and triethylamine to obtain 89 g of O-ethyl-S-n-propyl phosphorochloridothiolate. The purity was 89.3%. Therefore, the yield based on the total phosphorus was 78%.

It will be appreciated that the instant specification and examples are set forth by way of illustration and not limitation, and that various modifications and changes may be made without departing from the spirit and scope of the present invention.

We claim:

1. A process for the production of a phosphoro chloride thiolate of the formula

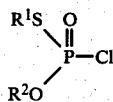

wherein
R$^1$ is alkyl, alkoxyalkyl, aryl, or aryl substituted by alkyl, alkoxy or halogen, and
R$^2$ is alkyl,
comprising reacting a mixture of a dialkyl chlorophosphite of the formula (R$^2$O)$_2$PCl and an alkyl dichloro phosphite of the formula (R$^2$O)PCl$_2$ substantially free of trialkyl phosphite of the formula (R$^2$O)$_3$P with a substantially quantitative amount of a sulphenyl chloride of the formula R$^1$SCl to produce a mixture of a phosphorochloridothiolate of the formula

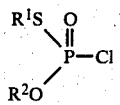

and a phosphoro dichloride thiolate of the formula

and reacting the mixture without isolation with an alcohol of the formula

R$^2$OH in the presence of a dehydrochlorinating agent thereby to convert the phosphoro dichloride thiolate of the formula

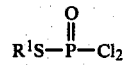

to additional phosphorochloridothiolate

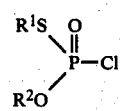

2. A process according to claim 1, wherein the mixture of dialkyl chlorophosphite and alkyl dichloro phosphite is produced by reacting a trialkyl phosphite of the formula (R$^2$O)$_3$P with about 0.6 to 1.5 times its molar amount of phosphorus trichloride at about −30° to 100° C.

3. A process according to claim 1, wherein the mixture of dialkyl chlorophosphite and alkyl dichloro phosphite is produced by reacting phosphorus trichloride with about 1.2 to 1.8 times the molar amount of an alcohol of the formula

R$^2$OH in the presence of a dehydrochlorinating agent and at about −30° to 100° C.

4. A process according to claim 1, wherein approximately equimolar amounts of the alcohol and the phosphoro dichloride thiolate in the mixture are reacted, and the dehydrochlorinating agent is thereafter employed in approximately the same molar amount at about −20° to +50° C.

5. A process according to claim 1, wherein the dehydrochlorinating agent is an alcoholate or a tertiary amine.

6. A process according to claim 1, in which
R$^1$ is methyl, ethyl, n- or iso-propyl, n-, iso-, sec- or tert-butyl, n- or iso-amyl, n-hexyl, methoxyethyl, ethoxymethyl, n- or isopropoxymethyl, n-, iso-, sec- or tert-butoxyethyl, 3-methoxypropyl, 3-ethoxypropyl, phenyl, naphthyl, or phenyl or naphthyl substituted by methyl, ethyl, n- or iso-propyl, n-, iso-, sec- or tert-butoxy, chlorine, fluorine, bormine and/or iodine, and
R$^2$ is methyl, ehtyl, n-iso-propyl, n-,iso-, sec- or tert-butyl, n- or iso-amyl or n-hexyl.

7. A process according to claim 6, wherein the reactions are effected in an inert diluent, approximately equimolar amounts of the alcohol and the phosphoro dichloride thiolate in the mixture are reacted, and the dehydrochlorinating agent is thereafter employed in approximately the same molar amount at about −20° to +50° C., the dehydrochlorinating agent comprising an alcoholate or tertiary amine.

* * * * *